(12) United States Patent
Berreklouw

(10) Patent No.: US 8,366,766 B2
(45) Date of Patent: Feb. 5, 2013

(54) ASSEMBLY COMPRISING A RING FOR ATTACHMENT IN A PASSAGE SURROUNDED BY BODY TISSUE AS WELL AS AN APPLICATOR FOR FITTING THE RING IN THE PASSAGE

(75) Inventor: Eric Berreklouw, Son (NL)

(73) Assignee: Daidalos Solutions B.V., JN Son (NL)

( * ) Notice: Subject to any disclaimer, the term of this patent is extended or adjusted under 35 U.S.C. 154(b) by 1252 days.

(21) Appl. No.: 10/594,363

(22) PCT Filed: Mar. 29, 2005

(86) PCT No.: PCT/NL2005/000230
§ 371 (c)(1), (2), (4) Date: Jul. 2, 2008

(87) PCT Pub. No.: WO2005/092246
PCT Pub. Date: Oct. 6, 2005

(65) Prior Publication Data
US 2008/0281411 A1    Nov. 13, 2008

(30) Foreign Application Priority Data
Mar. 26, 2004   (NL) ..................................... 1025830

(51) Int. Cl.
  *A61F 2/24*   (2006.01)
(52) U.S. Cl. ...................... 623/2.11; 623/1.24; 623/2.13; 623/2.36; 623/2.37; 623/2.38; 606/142; 606/144; 606/153; 606/155; 606/219
(58) Field of Classification Search .................. 623/2.11, 623/2.13, 2.36, 2.37, 2.38; 606/142, 144, 606/151, 153, 155, 219
See application file for complete search history.

(56) References Cited

U.S. PATENT DOCUMENTS

| 4,485,816 A | 12/1984 | Krumme |
| 5,891,160 A | 4/1999 | Williamson, IV et al. |
| 5,964,770 A | 10/1999 | Flomenblit et al. |

(Continued)

FOREIGN PATENT DOCUMENTS

| EP | 0 896 813 A2 | 2/1999 |
| EP | 1 088 529 A2 | 4/2001 |

(Continued)

*Primary Examiner* — Vy Q Bui
(74) *Attorney, Agent, or Firm* — Abelman, Frayne & Schwab

(57) ABSTRACT

The present invention relates to an assembly comprising: a ring having anchoring elements for attaching the ring in a passage surrounded by body tissue, in particular blood vessel tissue. An applicator for fitting the ring in the passage; in which the anchoring elements have an anchoring position in which they protrude with respect to the ring, and in which the anchoring elements comprise a memory material, such as a memory metal or memory polymer, and are designed so that they can be bent from an anchoring position counter to a spring force into a fitting position and can be frozen in this fitting position by a temperature treatment in order to bend the anchoring elements back from the fitting position by the effect of this spring force into the anchoring position when a predetermined threshold temperature is exceeded, and in which the applicator is provided distally with a carrier for carrying the ring. The assembly according to the invention is provided with an influencing system for influencing the temperature of the anchoring elements of the ring carried by the carrier in such a way that the anchoring elements bend back from the fitting position to the anchoring position by increasing the temperature of the anchoring elements to above the threshold temperature.

22 Claims, 10 Drawing Sheets

U.S. PATENT DOCUMENTS

| | | | |
|---|---|---|---|
| 6,491,704 B2 * | 12/2002 | Gifford et al. | 605/153 |
| 7,311,730 B2 * | 12/2007 | Gabbay | 623/2.38 |
| 7,524,330 B2 * | 4/2009 | Berreklouw | 623/1.36 |
| 2002/0029049 A1 | 3/2002 | Gifford, III et al. | |
| 2003/0149476 A1 | 8/2003 | Damm et al. | |
| 2005/0033393 A1 | 2/2005 | Daglow | |
| 2009/0216115 A1 * | 8/2009 | Seiler et al. | 600/426 |

FOREIGN PATENT DOCUMENTS

| | | |
|---|---|---|
| WO | WO0024339 | 5/2000 |
| WO | WO 00/44311 A3 | 8/2000 |
| WO | WO 03/003926 A1 | 1/2003 |
| WO | WO03003926 | 1/2003 |
| WO | WO03082121 | 10/2003 |

* cited by examiner

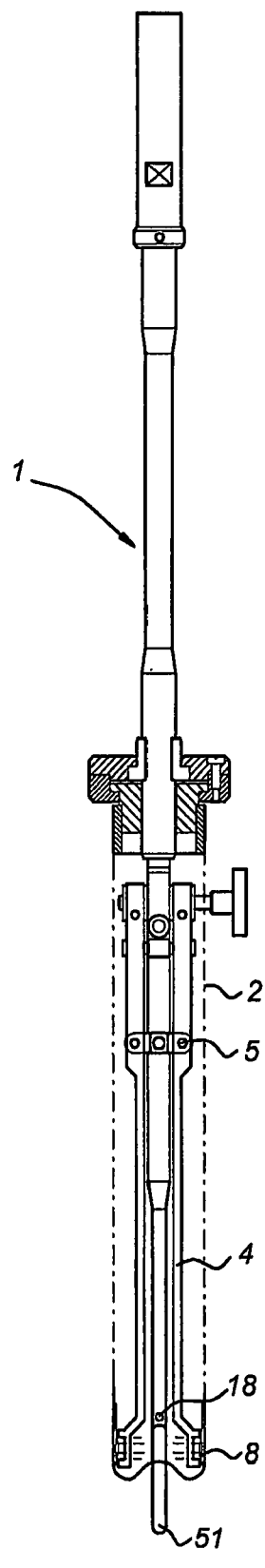
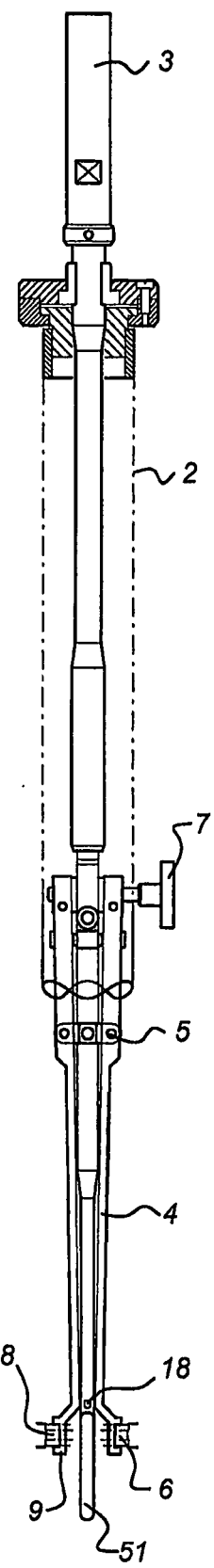

ASSEMBLY COMPRISING A RING FOR ATTACHMENT IN A PASSAGE SURROUNDED BY BODY TISSUE AS WELL AS AN APPLICATOR FOR FITTING THE RING IN THE PASSAGE

The present invention relates to an assembly comprising:
a ring having anchoring elements for attaching the ring in a passage surrounded by body tissue, in particular blood vessel tissue.
an applicator for fitting the ring in the passage;
in which the anchoring elements have an anchoring position in which they protrude with respect to the ring, and
in which the anchoring elements comprise a memory material, such as a memory metal or memory polymer, and are designed so that they can be bent from an anchoring position counter to a spring force into a fitting position and can be frozen in this fitting position by a temperature treatment in order to bend the anchoring elements back from the fitting position by the effect of this spring force into the anchoring position when a predetermined threshold temperature is exceeded; and
in which the applicator is provided distally with a carrier for carrying the ring.

In the context of this application "freeze", "frozen", etc. is understood in a general sense to mean fix, fixed, etc. into a position which is released when a specific threshold temperature is exceeded. In this context, neither the value of the threshold temperature, nor the temperature/temperatures at which the heat treatment takes place are specified. These are dependent on the composition/properties of the specific materials used. In this context, freezing does thus not really refer to the physical concept of solidification.

An applicator of this type is known from NL 1018302 and from NL 1020288, WO 03/082121 and WO 03/003926, all four in the name of the Applicant.

In addition, various applications by the Applicant, such as WO 00/24339 and WO 00/44311, disclose attachment devices comprising an annular element—usually referred to as a tubular element in said WO publication—with anchoring elements—usually referred to as flanges or flange legs in said WO publications—comprising a memory material. These attachment devices have movable anchoring elements on the underside in combination with a fixed flange on the upper side or likewise movable anchoring elements on the upper side. These anchoring elements have an anchoring position in which they protrude with respect to the ring and can be bent from this anchoring position counter to a spring force into a fitting position and can be frozen in this fitting position by means of a temperature treatment. As is known of memory materials, the anchoring elements will return to the anchoring position by the effect of the spring force when a predetermined threshold temperature is exceeded. This characteristic of memory material, i.e. that they can be bent from a first position into a second position, can be frozen into this second position by a temperature treatment in order to bend back into the first position when a threshold temperature is exceeded, is widely used in the medical field, such as with stents, in orthodontics, etc. This effect of memory materials is thus widely known.

EP-1,088,529-A2 discloses an assembly comprising a catheter and a foldable prosthesis comprising a foldable ring structure. The prosthesis is folded up inside the catheter. One brings the prosthesis to its destination inside the body by means of the catheter. The prosthesis is moved out of the catheter and then unfolded. Subsequently projections are forced to open outwardly and penetrate into the vassal wall. The prosthesis comprises a shape memory material to accomplish unfolding of the ring by heating up to 50° C. and deploying of the projections by heating up to 60° C. Heating is accomplished by using a balloon in which hot water is introduced.

US 2003/0149476 discloses a heart value prosthesis which is implantable by means of a catheter. During introduction through the aorta the catheter is folded up inside the catheter. The prosthesis is provided with hook-shaped anchoring elements made of a form storage metal which maintains that the elements sit flat during the phase of introduction. Erecting of the hooks will occur at the site of implantation. In case a balloon catheter is used, the balloon can also be used for cooling. Erection of the hooks will occur after switching of the cooling means. The hooks will erect after assuming the body temperature.

EP 896.813 A2 concerns elements for anchoring implant devices. Passing of those elements from the retracted to the expanded position is achieved by virtue of a shape memory mechanism. The prosthesis is put in place by catheterisation and for this purpose mounted in well known manner in a catheter. In order to reach a predetermined transition temperature, the anchoring elements are heated or, in theory, can be cooled. In case of heating, the anchoring elements pass from retracted to expanded position because the temperature in increased to transition temperature. In case of cooling the memory mechanism functions exactly opposite. The anchoring elements pass from retracted to expanded position because the temperature is decreased to transition temperature.

In particular when heart valve prostheses are being fitted, but also when anastomoses are being performed, it is extremely important that the anchoring is very reliable and accurate.

It is an object of the present invention to provide an assembly of the type mentioned in the introduction with which a very accurate and reliable fitting of a ring provided with anchoring elements into a passage surrounded by body tissue, in particular blood vessel tissue, is possible.

This object is achieved with the assembly of the type mentioned in the introduction by the fact that the assembly is provided with an influencing system for influencing the temperature of the anchoring elements of the ring carried by the carrier in such a way that the anchoring elements bend back from the fitting position to the anchoring position by increasing the temperature of the anchoring elements to above the threshold temperature. A temperature-influencing system of this type enables a controlled release of the anchoring elements—after which they bend back from the fitting position into the anchoring position—by allowing the temperature of the anchoring elements to rise in a controlled manner above the threshold temperature by means of the influencing system.

In order to reliably prevent one or more anchoring elements from returning from the fitting position to the anchoring position prematurely, for example by locally exceeding the threshold temperature, it is advantageous in this case if the influencing system comprises a cooling device for cooling the anchoring elements to a temperature below the threshold temperature. In this context, the term cooling should be regarded primarily as relative to the threshold temperature. For example, if the threshold temperature is about 30° C., a device which maintains the temperature of the anchoring elements at 25° C. can already be regarded as a cooling device. However, this does, of course, not alter the fact that the cooling device may also cool to much lower temperatures, such as for example to refrigerator temperature or even lower.

In order to reliably ensure that all anchoring elements bend back from the fitting position to the anchoring position, also referred to as turning over, it is advantageous according to the invention if the influencing system comprises a heating device for heating the anchoring elements to a temperature above the threshold temperature. In this case too, it should be mentioned that the term heating device relates primarily to the threshold temperature. A heating device which heats up to maybe a few degrees above the threshold temperature should in this context already be seen as being a heating device, even if the threshold temperature is very low.

In order both to ensure that the anchoring elements cannot turn over prematurely from the fitting position to the anchoring position, and to ensure that the anchoring elements are all turned over to the anchoring position at a specific desired moment, it is very advantageous according to the invention, if the influencing system comprises a cooling device as well as a heating device.

According to a further advantageous embodiment, the part of the carrier contacting the ring is made of a heat-conducting material, such as for example metal, and the influencing system is connected in a heat-exchanging manner to that part of the carrier contacting the ring or the influencing system even forms part of the carrier. In this way, it becomes possible to adjust the temperature of the ring and the anchoring elements by adjusting the temperature of the carrier. In this case, the carrier can be designed in such a manner that it contacts the anchoring elements which are in the fitting position in order to influence the temperature thereof more directly, in particular in order to be able to keep these anchoring elements at a temperature below the threshold temperature.

According to a further embodiment, the influencing system on the assembly according to the invention may comprise a Peltier element. A Peltier element is an electrical element which is known as such from the prior art and which, when subjected to direct current, has a cold side and a warm side. In this case, the temperature difference between the warm and the cold side can be controlled. In addition, the cold side and the warm side can be reversed by reversing the polarity. In general, a Peltier element is composed of a number of semi-conductor components, also known as p-n junctions, which are mounted between two ceramic panels acting as electrical insulators. If an electric current flows in one direction, heat is conveyed from one side of the semiconductor components to the other side. Reversing the direction of flow/polarity likewise results in a reversal of the conveying direction of the heat.

The influencing system of an assembly according to the invention may comprise a channel for supplying a fluid, such as a liquid or gas, to the carrier, optionally in combination with a Peltier element. Examples of fluids which can then be used in order to cool to below the threshold temperature are cold water, or cold gaseous $CO_2$, $N_2$ (nitrogen) or $N_2O$ (laughing gas). Carbondioxyde, nitrogen or laughing gas in liquid form are likewise possible as cooling fluids. In order to heat to above the threshold temperature, use can be made of, for example, warm water or a warm gas.

According to a further embodiment, the influencing system may comprise a source for generating an alternating electromagnetic field, in which case the carrier and/or the ring and/or the anchoring elements are designed in such a manner that they are sensitive to heating by this alternating electromagnetic field. It is generally known to those skilled in the art that a material in which free electrons are present, can be heated by subjecting it to an alternating electromagnetic field. A microwave oven and induction cooking are both based on this principle. This principle makes it possible to heat an object by means of an electromagnetic field from a certain distance without involving direct contact. This is advantageous with the present invention, since hardly any arrangements have to be made on the applicator, except for the fact that the carrier of the applicator is optionally made of a material which is suitable for heating by the effect of an alternating electromagnetic field. However, instead of the carrier or in addition to the carrier, it is also possible to make the ring and/or anchoring elements of a material which can be heated by the effect of an alternating electromagnetic field.

With an influencing system comprising a source for generating an alternating electromagnetic field according to the invention, it is advantageous if the source has at least one electrically conductive loop which can be connected to an alternating current source. This at least one loop may thus also comprise a multiplicity of loops wound to form a coil. The advantage of such a loop structure is that is that it produces an extremely concentrated alternating electromagnetic field in the plane of the loop, which is still highly concentrated just in front of the loop. In this case, according to the invention, it is particularly advantageous if the loop has a passage of a size such that the ring can be accommodated therein with play, the size of the passage preferably being at least 1.2 times larger than that of the ring. In this manner, it is possible to place the loop around the ring with anchoring elements, or optionally above, such as just above, or optionally below, such as just below, this ring, it being possible for the loop to be situated on the outside around the blood vessel tissue into which the ring has to be fitted. It is also possible to situate the loop advantageously next to the blood vessel tissue into which the ring has to be fitted.

According to a further advantageous embodiment, the composition of the material of the anchoring elements is chosen such that the threshold temperature is around or below the human body temperature. Choosing the threshold temperature to be around or below the human body temperature prevents the anchoring elements from in any way being frozen in a position other than the anchoring position afterwards, i.e. after surgery, that is to say prevent this from happening inadvertently. A further advantage of choosing the threshold temperature to be around or below the human body temperature is that the heating means do not require to be heated to a temperature which might damage the human body locally. The threshold temperature will according to the invention in particular be lower than or equal to 37.5° C. More particularly, the threshold temperature according to the invention will in particular be lower than the body temperature; in particular a few degrees lower than the body temperature, such as for example lower than or equal to 34.5° C.

With regard to the threshold temperature, it should be pointed out that with memory materials, such as memory metals, for example Nitinol or plastics with memory properties, there usually is a temperature range within which the transition from the temporary shape—the fitting position—to the final shape—the anchoring position—takes place. With memory metals, a distinction is drawn essentially between four temperatures. Progressing from a low to a high temperature, these are the Martensitic finish temperature, abbreviated Mf, the Martensitic start temperature, abbreviated Ms, the Austenitic start temperature, abbreviated As, and the Austenitic finish temperature, abbreviated Af. There are usually a few degrees C. (for example approx. 5°) between the Martensitic finish temperature and the Martensitic start temperature, as well as between the Austenitic start temperature and the Austenitic finish temperature (for example approximately 10° C.), and there may again be a few degrees (for example 8° C.) between the Martensitic start temperature and the Austenitic start temperature. As is known from practice, there may be a difference of more than 20° C. between the Martensitic finish temperature and the Austenitic finish temperature. What temperatures these are exactly depends on the composition of the material and is, as those skilled in the art know, selectable by choosing the correct material composition and temperature shape setting. At temperatures below the Martensitic finish temperature—having started from relatively high temperatures—an object has definitely reached its temporary shape. Please note that this is independent of deformability as the material can still be deformable. Having started from relatively high temperatures, an object will begin to take on its temporary shape when the Martensitic start temperature is transgressed. Progressing from a low to a high temperature, an object with a temporary shape will start to take on its final shape when the Austenitic start temperature is exceeded and will have taken on/take on its final shape when the Austenitic finish temperature is exceeded. In addition, a distinction is drawn between a one-way effect and a two-way effect. With the one-way effect, when heated above As temperature, the material actively takes on the Austenitic shape which becomes final above Af temperature, but does not automatically take on a temporary Martensitic shape when it cools down to below the Ms temperature. The material does start to become deformable, at its most below the Mf temperature. With the two-way effect, or bi-stable memory materials, the material actively takes on the Austenitic shape when heated to above the As temperature and the Martensitic shape when it cools down to below the Ms temperature.

In the opinion of the Applicant, the threshold temperature covers a temperature range between the Austenitic start temperature (As temperature) and the Austenitic finish temperature (Af temperature). The term "threshold temperature" is understood to mean the temperature at which the material takes on its final shape and thus includes the entire temperature range between the Austenitic start and finish temperatures. This range may in practice be, for example, 10° C. If one would like to indicate one threshold temperature, this would be the temperature at which the final shape is achieved and at which it can be guaranteed that this shape will be maintained in the body under normal physiological temperatures. In the opinion of the Applicant, this threshold temperature would then have to be the Austenitic finish temperature.

According to a further advantageous embodiment of the invention, the influencing system, especially its heating device, is designed to raise the temperature of the anchoring elements to approximately 10 degrees (+/−5 degrees) C. above the threshold temperature. According to a further advantageous embodiment of the invention, the influencing system, especially its cooling device, is designed to lower the temperature of the anchoring elements to approximately 20 degrees (+/−5 degrees) C. below the threshold temperature and optionally maintain it there.

According to a further advantageous embodiment of the assembly according to the invention, the carrier comprises gripper parts which can be moved between a position gripping the ring and a position releasing the ring. In this context, this may in particular involve the following possibilities:

the gripper parts can be moved radially between a position gripping the ring from the inside and a position releasing the ring; and/or the gripper parts can be moved in the longitudinal direction between a position gripping the ring from above and/or below and a position releasing the ring.

In the case of an animal valve prosthesis which is attached to the ring beforehand, it is particularly advantageous according to the invention if the gripper parts can move in the longitudinal direction between a position gripping the animal valve prosthesis from above and/or from below and a position releasing the animal valve prosthesis from above and/or from below. With all these ways of the gripper parts acting on the ring, the ring is left clear on the outside, so that the gripper will not interfere with the anchoring elements. The gripper parts may also act on a fixed top flange. In this case, the gripper parts can not only grip such a top flange from above, but also from the side in the horizontal plane and be moved. This applies in particular to vessel attachment devices which are designed in this way and around which there is generally sufficient space.

According to a further advantageous embodiment, the applicator comprises a sleeve which can slide along the applicator between a position overlapping the ring provided on the carrier and a position exposing the ring provided on the carrier. Thus it is possible to protect the ring with anchoring means against the outside so that it does not come into contact with surrounding tissue when this ring with anchoring means is being brought into the intended position inside the passage surrounded by body tissue. If an anchoring element frozen in its fitting position were to get caught behind tissue, this anchoring element could bend over and damage tissue.

In order to facilitate bringing the ring with anchoring means into its intended position inside a passage surrounded by tissue, in particular via the bloodstream, it is very advantageous according to the invention, if the sleeve comprises a distal part which may or may not be fixedly connected to it or form an integral part thereof and tapers in the distal direction to form a diameter which is smaller than that of the ring, and if that distal part consists of axial fingers which can bend radially outwards from the tapering position in such a manner that this tapering part of the sleeve can be displaced over the ring, in particular over the distal anchoring elements in the fitting position and, if appropriate, also over the proximal anchoring elements. The distal tapering part may for example taper conically, but may also taper parabolically. This tapering considerably eases navigation to the intended position. However, the tapering part will have to be removed before the anchoring elements are released from the fitting position to the anchoring position. In order to remove this distal tapering part without interfering with the ring, it is very advantageous if this distal part consists of axial fingers which can move outwards, for example can bend, in such a manner that this tapering part of the sleeve, also referred to as head, can be displaced over the ring. The distal tapering part may be placed over the sleeve from the proximal or from the distal direction or may form an integral part thereof, but will, generally after the applicator has been navigated to the intended position, have to be removed in the proximal direction. With a ring having a fixed top flange or anchoring means which are already in the fitting position or fixed proximally, such a tapering part can only be moved up via or from the sleeve from the proximal direction. Such a tapering head on the distal part of the sleeve enables the use of the assembly via a guide wire, especially if the central section of the applicator is designed to be hollow. In addition, the sleeve or the tapering part thereof may be provided with parts extending in the radial direction or a ring extending in the radial direction, which parts or ring, respectively, may serve to rest on the surrounding (vessel) tissue. Such parts extending in the radial direction could, for example, be arranged on the sleeve or the tapering part thereof in such a manner that they occupy a position on the outside of the sleeve or the tapering part thereof with respect to the ring, which is such that the ring is positioned at the desired distance with respect to the anatomical structures on which they rest. This results in the navigation of the assembly being facilitated as such parts can act as a plug and even blind navigation becomes possible.

In a ring with anchoring elements, in which the proximal anchoring elements are designed to be completely or partially fixed or have been brought into an anchoring position beforehand, while the distal anchoring elements can be brought into and maintained in a fitting position, as is known from various applications by the inventor, inter alia WO 00/24339 and WO 00/44311, it is furthermore advantageous to provide the sleeve with incisions, creating axial fingers, in such a manner that the sleeve can be positioned around the ring and distal anchoring elements by displacing these fingers in the longitudinal direction between proximal (fixed) anchoring elements, the incisions being situated at the location of the proximal anchoring elements.

According to a further embodiment of the invention, the sleeve is provided at its distal end with axial fingers and the ring is provided at its distal end with such anchoring elements, a space being left between neighbouring axial fingers and the axial fingers being provided in such a manner that, when the ring is accommodated in the sleeve, each axial finger overlaps a respective distal anchoring element. Thus it is possible for further anchoring elements, for example proximal anchoring elements, to protrude permanently in the radial direction via the spaces between the axial fingers or that such further, for example proximal, anchoring elements are brought into a protruding position before the distal anchoring elements. According to a further advantageous embodiment, the ring is in this case provided at its proximal end with a flange which extends radially outwards for interaction with the distal anchoring elements, and this flange is provided with passages for those axial fingers. In this case, the flange may be an uninterrupted flange which runs entirely around the outside of the axial fingers and has slots on its inner side for enabling the axial fingers to pass through. According to another embodiment, it is also possible in this case for the ring to be provided with these anchoring elements at its proximal end and for these proximal and distal anchoring elements to be provided in a staggered manner with respect to each other, seen in the tangential direction to the ring, in such a manner that the axial fingers can overlap with the distal anchoring elements when they protrude through the proximal anchoring elements, it furthermore optionally being advantageous if the proximal anchoring elements are in an extended state inside the part of the sleeve which is proximal with respect to the axial fingers.

In a further advantageous embodiment, the proximal and distal anchoring elements surround the ring in an alternating manner, seen from above or below. Alternatively, gaps can be made in the fixed proximal anchoring element or in the fixed proximal anchoring elements, which describe part of a circle, as a result of which the axial fingers can be displaced in the longitudinal direction. These axial fingers can also be of tapering design, as described before above.

According to a further advantageous embodiment of the assembly according to the invention, the applicator can be provided with parts which can be used to connect to a stabilizer, which can be connected, for example, to a sternum spreader, operating table, or fixed part of or in the operating theatre, as is known from previous applications by the inventor.

According to a further advantageous embodiment of the assembly according to the invention, the applicator, gripper arms, and/or the sleeve is/are designed to be flexible in order to facilitate the introduction and navigation of the assembly. According to another advantageous embodiment, these components of the assembly, separate from or in addition to the flexible embodiment, can be of perforated design. Thus it is possible to move the assembly up in the bloodstream, optionally while the heart is beating, without impeding the blood flow too much.

According to a further advantageous embodiment of the assembly according to the invention, the ring is provided with a valve prosthesis, which may or may not be detachable, in particular a heart valve prosthesis. In case the valve prosthesis comprises one, two or more valve leaflets, it is very advantageous according to the invention if the carrier is provided with a longitudinal member extending in the longitudinal direction, which may extend through the ring and against which the valve leaflets of the valve prosthesis supported by the carrier rest in their open position. Thus it is ensured that the valve leaflets are kept in an open position in the longitudinal direction while they are being transported to the intended position in order thus to prevent damage to those valve leaflets.

According to a further advantageous embodiment of the assembly according to the invention, the ring is provided with anchoring elements for attaching a valve prosthesis to the ring. This valve prosthesis may be attached to the ring prior to the introduction of the ring into the body, but may also be attached to the ring after the ring has been positioned and fastened in the passage surrounded by body tissue. If desired, these anchoring elements may be released or removed or replaced if a valve (ring) prosthesis needs to be removed and, if desired, to be replaced with another valve prosthesis, without removing the ring with (tissue) anchoring elements. If the anchoring elements for attaching the ring to the tissue and/or for attaching a valve prosthesis to the ring are made of bi-stable Nitinol, it is possible to remove the entire ring from the tissue and/or only the valve prosthesis from the ring more easily after cooling.

According to yet a further embodiment of the invention, the ring is a valve reconstruction ring. The term valve reconstruction ring is to be understood as meaning in particular a ring which is attached in the bloodstream along the surrounding vessel wall tissue in a natural heart valve in order to narrow the passage at the location of the valve without removing the valve leaflets. The purpose thereof is to repair a heart valve which is defective or not functioning well due to a local dilatation, or to make it function well again.

According to yet a further embodiment of the invention, the ring is an anastomosis attachment device. In this context, reference can be made to various embodiments as described in previous patent applications in the name of the Applicant, such as WO 00/24339 and WO 00/44311.

According to yet a further embodiment of the invention, the ring is provided with anchoring elements for attaching a cannula and/or port and/or operating channel. Possibilities of this kind are described in the aforementioned WO 00/44311, see for example FIGS. 40 and 53, by the inventor.

According to yet a further embodiment of the invention, the assembly can be combined with a vacuum stabilizer which is positioned at the location of and/or around the passage in the (vessel) tissue, where the ring is to be positioned, thus facilitating the navigation or forming a bloodless operating channel, or stimulating tissue contact. Vacuum stabilizers of this type are described in previous applications in the name of the Applicant, such as NL 1020288 and WO 03/082121.

According to the invention, it is furthermore advantageous if the assembly is fitted with one or more sensors and/or one or more marks distally, in particular near the carrier. Sensors and/or marks of this type make it easier not only to navigate the distal end of the assembly to the intended position, but also to accurately position the ring at the intended position.

According to a further aspect, the invention relates to an applicator suitable for an assembly according to the invention.

According to yet a further aspect, the invention relates to a ring suitable for an assembly according to the invention. The ring for the assembly according to the invention respectively the ring of the assembly according to the invention concerns especially a non-foldable ring (in contrast to stent like rings which can be folded up to have a considerable smaller diameter).

This application further relates to a second invention, which is the subject of claims 31-34. This second invention can be applied separate from the first invention (claims 1-30) or in combination with the first invention.

For a good heart valve prosthesis there are two important requirements. It must be reliably secured to the surrounding body tissue and the prosthesis may not leak. Concerning leakage, applicant noticed that vessel tissue, such as valve annulus tissue, can, especially in case of weak tissue, expand on long term with the result that the valve prothesis is loosening and that leakage around the prosthesis becomes possible.

The second invention has as its object to provide a heart valve prosthesis overcoming this objection. This object is achieved by providing a heart valve prosthesis according to claim 31. The constriction system having pins moving in radially inward direction, after having penetrated the tissue, ensure that the surrounding body tissue, in general vessel tissue, such as annulus tissue, has improved contact with the ring member. The pins tend to constrict the body tissue while moving inward. This does not only reduce the long term risk of leakage but also improves the sealing on short term. In case the ring or other parts of the valve prothesis are provided, for example covered, with a material enhancing ingrowth of tissue, the sealing by ingrowth of tissue is improved as well.

For the skilled man it will be clear that the required movement of the pins from the first penetrated to the second penetrated position can be achieved in various manners or various combination of manners.

One of the manners is using spring force. In this respect the embodiment according to claim 32 of the second invention is advantageous. According to this embodiment one can use a mechanical restriction, such as retractable pens or strips, to keep the pins temporarily in the first penetrating position. But one can also make use of memory metals or plastics (as already extensively described in relation to the first invention), which can be, so to say, frozen in the first penetrating position to be released to go back to the second position when the temperature increases above a certain threshold temperature.

Another manner is to arrange the pins on a carrier which can be shortened to move the pins in said radially inward direction. In this way it is possible not to bend the pins but just to move them radially, although additionally bending the pins is possible as well. Such a carrier can comprise a radial arm for each pin, which radial arm can be shortened for example by making use of memory effects of so called memory metals or plastics. The carrier can also comprise a ring which can be reduced in diameter, for example by making use of memory effects of so called memory metals or plastics.

The constriction system can, according to claim 34, comprise a ring element which can be separate from the ring member. Such a constriction system can be deployed at its location before the remainder of the prosthesis is deployed. This makes it possible to restrict the body tissue to a diameter smaller than required for the ring member. This ensures a tight fitting with the ring member, decreasing the risk of leakage.

The present invention will be described in more detail below with reference to the examples illustrated in the drawing, in which:

FIG. 1 diagrammatically shows an assembly according to the invention, in a state in which it is suitable for being taken to the intended position in the body;

FIG. 2 is a similar view to that of FIG. 1, except that the assembly is now in a position in which the ring with the anchoring elements is in the anchoring position and is released by the applicator;

Figure 13A:
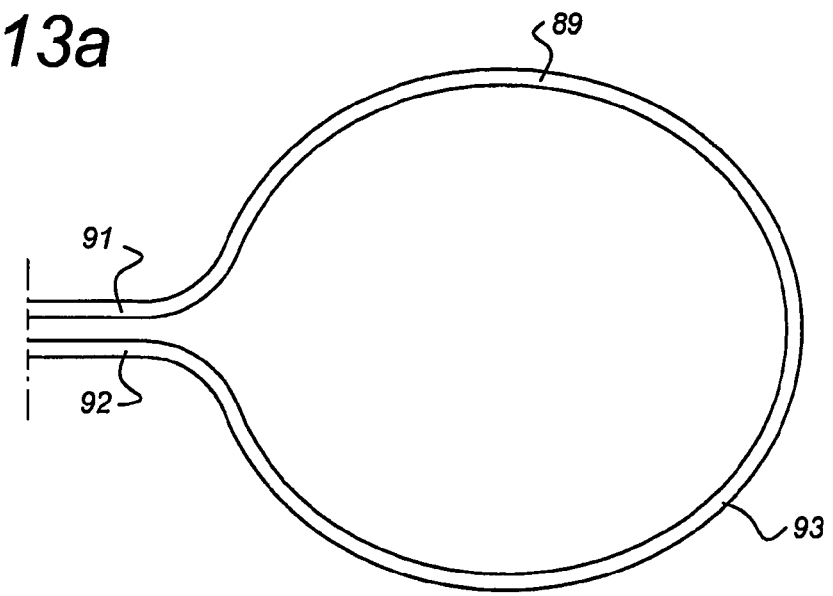
Figure 13B:
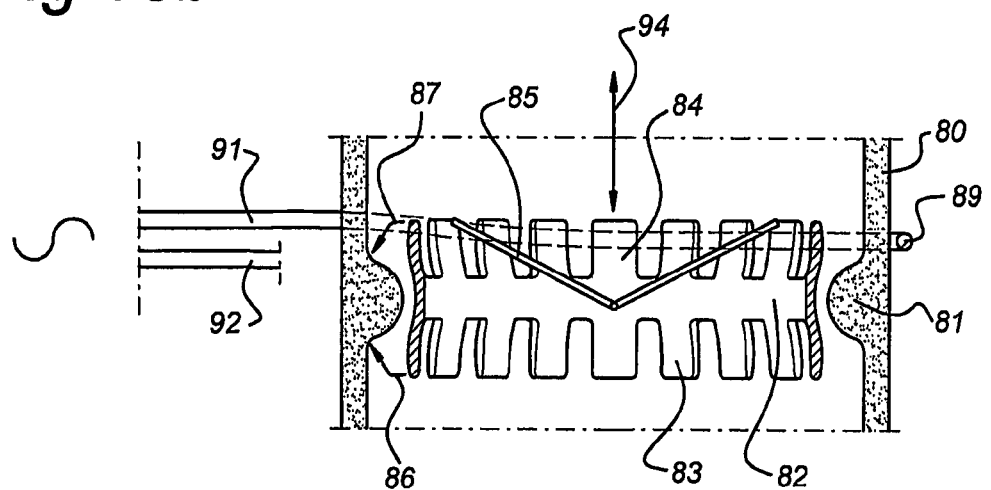
Figure 14:
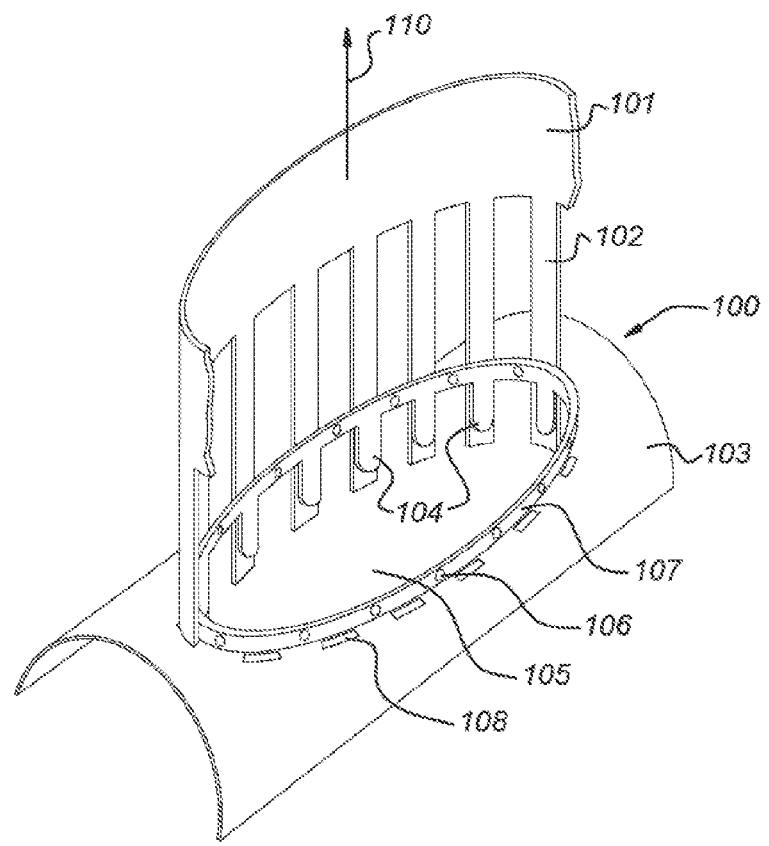
Figure 17:
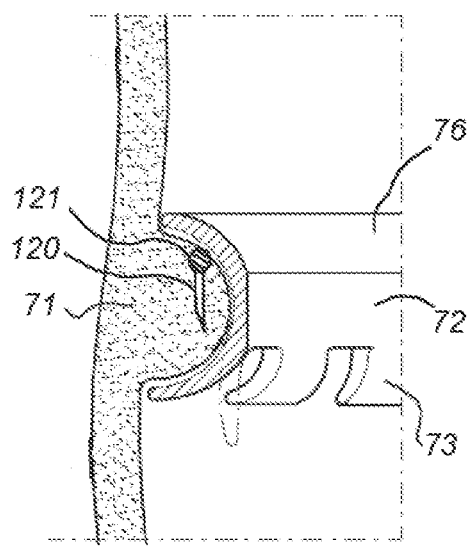

FIG. 13 diagrammatically shows an example of an influencing system working with an electrostatic field, with FIG. 13a showing a diagrammatic plan view of a loop for generating an electrostatic field and FIG. 13b showing a diagrammatic sectional view of a section of blood vessel tissue with an artificial heart valve to be fitted;

FIG. 14 shows a diagrammatic perspective view of a variant of the device from FIGS. 11 and 12, but in this case used in a fastening device for an end-to-side anastomosis;

FIG. 15 shows in sectional view an embodiment of the second invention of this application;

FIG. 16 shows diagrammatically another embodiment of the second invention of this application; and FIG. 17 shows in sectional view another embodiment of the second invention of this application.

Figure 4:
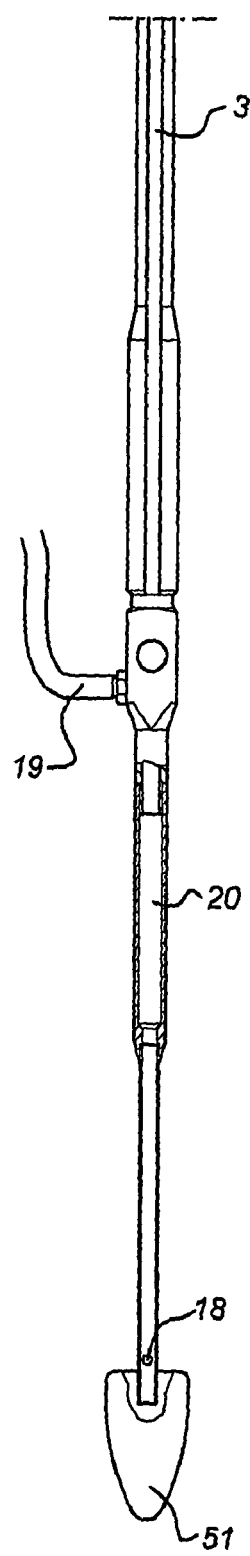
FIG. 4 shows a diagrammatic view of the central section of the applicator from FIGS. 1, 2.
Figure 5:
FIG. 5 shows a diagrammatic view of one of the grippers of the applicator from FIGS. 1 and 2.

The present invention relates to an assembly consisting of an applicator and a ring with anchoring elements as well as separately to the applicator on the one hand and the ring on the other hand. An assembly according to the invention is shown in FIGS. 1 to 5, with FIGS. 3, 4 and 5 showing the basic components of the applicator separately and FIGS. 1 and 2 the assembled applicator with a ring provided with anchoring elements.

The applicator 1 consists of an optional sleeve part 2 (see FIG. 3), also referred to as protective sleeve, a central section 3 and a number of, in this example two, grippers 4 (see FIG. 5), which together form the carrier.

As FIG. 2 shows, the grippers 4 are attached to the central section 3 so that they can pivot about pivot point 5. The grippers 4 are provided at their distal end with a recess 6 into which the ring of the assembly fits. By means of the adjusting screw 7 provided proximal from the pivot points 5, the proximal parts of the gripper arms 4 can be adjusted between a position shown in FIG. 1, in which the recesses 6 grip the ring 8 from the inside, and a position in which the proximal parts of the gripper arms are spread, the distal gripper ends 9 having accordingly been moved towards each other in order to release the ring 8 from inside, as is shown in FIG. 2. An applicator with gripper arms which function in a comparable manner is also shown in WO 03/082121, see inter alia FIGS. 3-6, in the name of the Applicant. The adjusting screw 7 has, as it were, been replaced in this case by a displaceable sleeve with recesses and gripper arms provided with protrusions which interact with the recess in the displaceable sleeve for bringing about a similar motion effect of the gripper arms. Within the scope of the present invention still to be described in more detail below, the applicator known from this WO 03/082121 could, after some modification in connection with the influencing system for the temperature, be used very well as an applicator for an assembly according to the present invention. In case the applicator is used in combination with valve or vessel attachment devices with fixed top flange, as is known, inter alia, from previous applications WO 00/24339 and WO 00/44311 by the inventor, the gripper arms may also act on the fixed top flange or features which have been fitted thereon from the outside inwards and/or from top to bottom. FIGS. 11, 12 and 14 show examples thereof.

Figure 3:
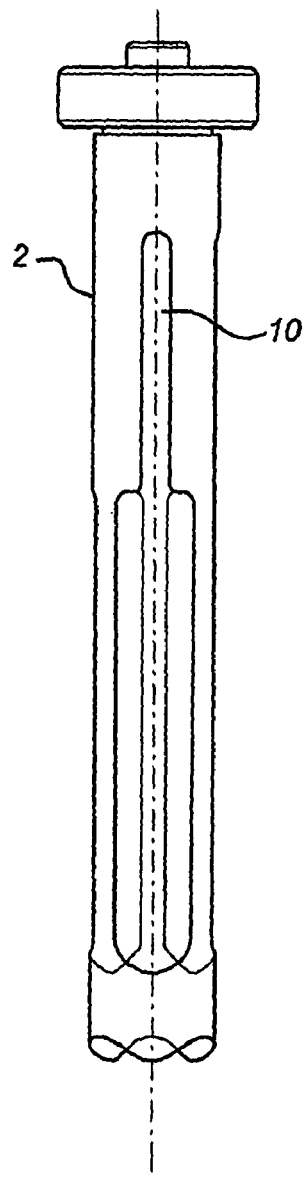
FIG. 3 shows a diagrammatic view of a protective sleeve for the applicator from FIG. 1.

The applicator in accordance with the assembly of the invention is optionally, but preferably provided with a sleeve 2 (shown separately in FIG. 3). As illustrated in FIGS. 1 and 2, this sleeve 2 is displaceable along the central section 3 of the applicator between a bottom or distal position and a top or proximal position. The sleeve 2 is provided with a slot 10 in order to enable the adjusting screw 7 to pass through. The purpose of the sleeve 2 is to protect the ring 8 with anchoring elements against the outside while the ring 8 with anchoring elements is taken to its intended position in the body. By way of further example, two different embodiments of a ring 8 with anchoring elements are illustrated in more detail in FIG. 9 and FIG. 10. As will become clear from the following description of these figures, the sleeve 2 protects the anchoring elements against the surrounding tissue, so that these anchoring elements cannot inadvertently get caught in this surrounding tissue. Furthermore, the sleeve 2 prevents the anchoring elements—as will become clear later on—from prematurely returning from a fitting position to the anchoring position in case the assembly does not function properly.

Figure 9:
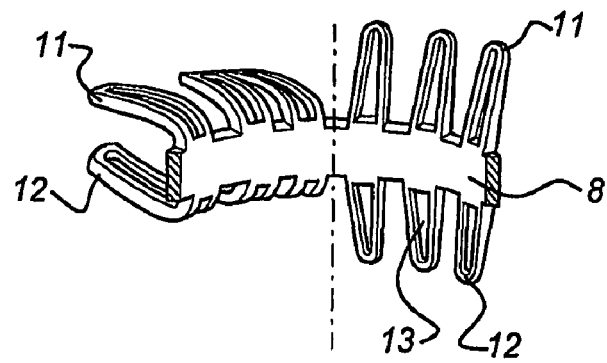
FIG. 9 shows an illustrative example of a section of a ring with anchoring elements in perspective view in which, by way of explanation, the anchoring elements are shown in the anchoring position on the left-hand side and in the fitting position on the right-hand side.

FIG. 9 shows an inside perspective view of a section of the ring 8 with anchoring elements 11 and 12. The left side shows the anchoring elements 11 and 12 in the anchoring position, while the right side shows the anchoring elements 11 and 12 in the fitting position. Anchoring elements 11 are on the proximal side of the ring 8 and anchoring elements 12 are on the distal side of the ring 8. In the fitting position, the anchoring elements 11 and 12 are, as it were, in their extended state and in the anchoring position shown on the left, they are in a state where they point radially outwards. Anchoring elements 11 may already be in a fitting position or permanently point in a radially outward direction prior to being fitted. It is also possible for the proximal anchoring element to be an uninterrupted radially outwardly pointing flange. The ring 8 and anchoring elements 11, 12 from FIG. 9 are made of a memory material, in particular a memory metal such as Nitinol or a memory polymer. In the initial position, the anchoring elements 11 and 12 here are in the anchoring position—shown on the left. From this anchoring position, the anchoring elements 11 and 12 can be bent counter to a spring force into the fitting position shown on the right. By means of a temperature treatment, the anchoring elements 11 and 12 can be frozen in this fitting position in such a manner that when a specific threshold temperature is exceeded, the anchoring elements 11 and 12, by the effect of the spring force—which had to be overcome when the anchoring elements were bent from the anchoring position to the fitting position—return to the anchoring position. Such an effect of memory metals and memory polymers is a well-known phenomenon as such.

The anchoring elements 11 and 12 shown in FIG. 9 are as it were lip-shaped and in each case provided with a recess 13. The recess 13 in the lip-shaped anchoring elements 11 and 12 may also be omitted, as can be seen in FIG. 10, for example. Here, anchoring elements 11 and 12 are shown which are all of identical shape, height and width and which are distributed evenly over the circumference of the ring. Particularly in the case of a vessel attachment device, which is used with a vessel of small diameter, such as a coronary artery, it may furthermore be advantageous if the anchoring elements 11 and/or 12, or a number of such elements, are of different shape, height and width, and/or are distributed unevenly over the circumference of the ring. In case of attachment to, for example, a small coronary artery, it may be desirable, in particular, to make the anchoring elements 12 longer and, if appropriate, also wider on the lateral sides of such a small vessel, while it may be advantageous to make these elements smaller or even omit them at the location of the axial inflow and/or outflow angles, in order to prevent, as much as possible, an obstruction of the blood flow at the location of the inflow and/or outflow angles.

The ring 8 with anchoring elements 11 and 12 as shown in FIG. 9 may be used for attaching a heart valve prosthesis inside a blood vessel, for example on the annulus at the location of the heart valve to be replaced. However, the ring 8 with anchoring elements 11 and 12 may also form part of a device for performing an anastomosis, for attaching a cannula, temporary port or operating channel to a blood vessel, To this end, a passage may be formed in the wall of the receiving blood vessel, the peripheral shape of which is identical to, or at least approximately identical to, the peripheral contour of the ring 8. The anchoring elements 11 and 12 can then be released from the extended fitting position, once the ring has been placed in this passage, in order to bend back to the anchoring position. In this anchoring position, the anchoring elements 11 and 12 will then act on the blood vessel wall from opposite sides. In the case of an end-to-side anastomosis, the ring is attached to the target vessel in this manner. Attachment of the graft vessel can be brought about in many different ways, either prior to attachment to the target vessel or subsequent to attachment to the target vessel. It is possible, for example, to suture the graft vessel to the ring 8 beforehand. Alternatively, it is possible to pull the graft vessel through the ring 8 beforehand and, together with the distal end, turn it over around the distal anchoring elements 12, so that the overturned part is pressed against the inside of the wall of the target vessel after the anchoring elements 12 have been bent back to the radially outwardly extending position. It is also possible to use a separate coupling piece at the location of the graft vessel, as is known from previous applications by the inventor. With a side-to-side anastomosis, a ring can be fitted in the wall of each of the vessels to be connected at the location of the opening in the wall, following which both rings, or the outer sides thereof, are connected to each other. If the vessel attachment device (that is to say, a device for attaching to a blood vessel in order to perform an anastomosis, comprising, like the assembly according to the invention, a ring with anchoring elements) is designed semi-cylindrically, both vessel attachment devices can be connected to one another, as it were forming one another's mirror image, with mutual contact and coupling elements being located around the passage, but according to an advantageous embodiment also as one another's parallel image, the contact, and if desired, the coupling elements extending over a much larger area. Any minor blood leaks around one or both rings will in this case be sealed by the other vessel attachment device. This is especially true for vessel attachment devices which use a fixed top flange. In this case, use can then also be made of the ring, top anchoring elements, but preferably the fixed top flange itself, or coupling elements connected to the latter, in order to bring about the actual coupling. For example, by bending over the outer edge of the fixed top flange of one of the two vessel attachment devices, a 'female' is created, into which the fixed top flange of the other vessel attachment device, the 'male', can be pressed. The use of two vessel attachment devices in parallel positions means that one of the two vessel attachment devices will not follow the cylindrically convex shape of the vessel wall, to which it is connected, but will, on the contrary, give it a mirrored concave shape. In coronary bypass surgery, for which this invention will inter alia be used, this does not in itself have to be a problem, as the situation which is usually encountered there, is that one of the two vessels in question is relatively large compared to the other vessel. It is obvious that the 'inverted' vessel attachment device can be connected to the relatively large vessel, so that there are no adverse effects for the blood flow at the location of the eventual vessel connection between the two vessels. It is also possible to use one ring at a time at the location of the opening in the wall of the two vessels to be connected, the anchoring elements 11 and 12 then being located on the inside of both vessels. Many other attachment techniques described in previous patent applications by the inventor can be applied here as well.

Figure 10A:
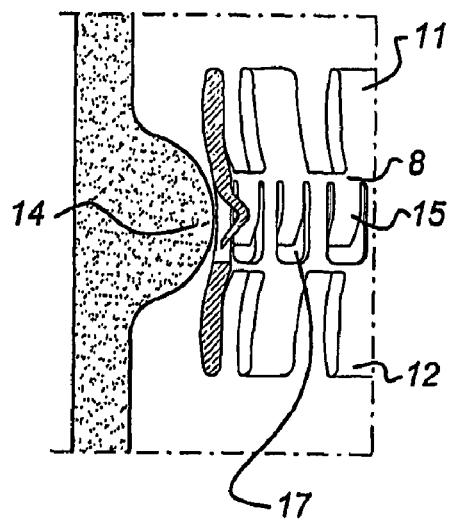
FIG. 10 shows, by way of example and with the entire applicator omitted, a ring with anchoring elements from the assembly according to the invention, with FIG. 10a showing the anchoring elements in the fitting position and FIG. 10b showing the anchoring elements in the anchoring position, namely at the location of the annulus of a heart valve.
Figure 10B:
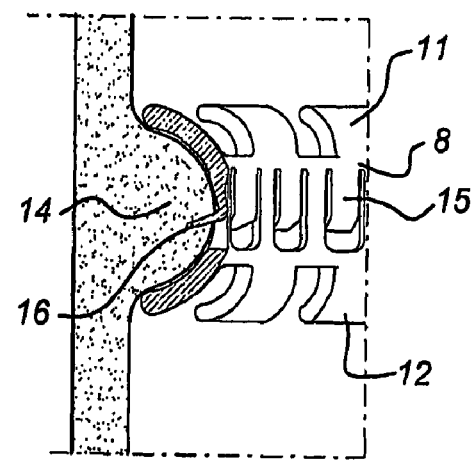

FIG. 10 shows, by way of further example, another ring with anchoring elements which can be used in combination with the assembly according to the invention. Here, identical parts have been given the same reference numerals as in FIG. 9. The ring is therefore again denoted by 8, the proximal anchoring elements by 11, the distal anchoring elements by 12. The ring 8 with anchoring elements 11, 12 shown in FIG. 10 is in particular intended for attachment inside a blood vessel on the annulus 14 at the location of a heart valve. The anchoring elements 11, 12, as shown in FIG. 10, are illustrated as closed lips, although the recesses 13 from FIG. 9 could be used here as well. A further difference with FIG. 9 is that the ring 8 is provided with yet further anchoring elements 15. The anchoring elements 15 are in the shape of L-shaped lips. FIG. 10a shows the ring 8 with anchoring elements 11, 12 and 15 in the fitting position, while FIG. 10b shows the ring 8 with anchoring elements 11, 12 and 15 in the anchoring position. As can be seen, in the anchoring position, the proximal anchoring elements 11 and distal anchoring elements 12 lie against the annulus 14 in order to clamp it. In the anchoring position, the anchoring elements 15 have penetrated the annulus 14 by means of the points 16. In order to keep the points 16 bent inwards in the fitting position, the ring 8 is provided with recesses 17 in which the L-shaped lips—which may be formed by punching—are accommodated. As for the manner in which the anchoring elements 11, 12 and 15 can temporarily be brought from the anchoring position into the fitting position, reference is made to the earlier description in connection with FIG. 9. Furthermore, it should be noted that the anchoring elements 15 in FIGS. 10a and 10b are shown as moving around a bending axis which is tangentially oriented with respect to the ring 8. However, it will be clear that these lips can also be rotated through 90° so that the bending axis is axially oriented with respect to the ring. In this connection, see also WO 00/44311 by the inventor.

The drawings show rings of an assembly according to the invention which have an essentially fixed diameter, a foldable ring might be conceivable as well.

The text which follows will deal more specifically with the present invention itself, namely with the influencing system provided on or near the applicator for influencing the temperature of the anchoring elements of the ring supported by the carrier in such a manner that the anchoring elements bend back from the fitting position to the anchoring position by increasing the temperature of the anchoring elements to above the threshold temperature. An influencing system of this type can be designed in many ways.

A relatively simple embodiment comprises a supply line 19 provided on the central section 3 (FIG. 4) for a fluid and a channel 20 formed in the central section 3 (FIG. 4) which connects the supply line to the distal part of the central section 3, and outflow openings 18 for the fluid provided on the distal part of the central section 3. These outflow openings 18 may be distributed distally over the circumference of the central section 3. The outflow openings 18 will preferably be provided or directed in such a manner that fluid emerging from them contacts the ring with anchoring elements as much as possible, that is at least the anchoring elements. The fluid may be, for example, a liquid, such as water or preferably a sterile saline solution, the temperature of which can be varied depending on whether the temperature of the anchoring elements has to be kept below the threshold value or rather has to be brought above the threshold value in order to cause the anchoring elements to bend back—also referred to as turning over. The fluid may also be gaseous, for example $CO_2$ or laughing gas. Such a fluid is routinely available in the operating theatre and has a very good cooling action. By means of such a gas, the anchoring elements can be kept at a temperature below the threshold temperature particularly reliably. If the threshold temperature then has to be exceeded in a controlled manner, it is easily possible to switch to a warmer fluid, such as for example a warm fluid which can be supplied via the same supply system 19, 20 and 18. The supply system 19 is shown here in the middle on the side of the central section of the applicator 3, but can be connected to the latter at another location, such as for example the proximal end of the central section 3.

As mentioned before, the influencing system for influencing the temperature of the anchoring elements may be designed in a different manner. Thus, it is conceivable to provide the gripper arms 4 with a channel system 21—diagrammatically indicated by dashed lines in FIG. 5—through which a fluid can be passed. This channel system 21 may optionally be provided with gripper arms 9 of an outflow opening similar to 18 at the distal end. However, it is very easily conceivable to provide the gripper arms 4 with a closed channel system and optionally to design the connecting port with two coaxial channels for supply and discharge. Fluid is then supplied to the distal end 9 of each gripper arm via this closed channel system and also discharged via the closed channel system via that end without allowing it to freely flow away. The temperature of the anchoring elements will then be controlled more indirectly, namely via the conduction of heat/ cold from the distal ends 9 of the gripper arms 4 to the ring 8 and/or anchoring elements 11, 12, 15. In particular if the ring 8 and the anchoring elements are made of metal and the distal gripper ends 9 of the gripper arms are likewise made of metal, this conduction of heat/cold can work very well.

Yet another possibility for an influencing system for the applicator could be the provision of cooling/heating elements, such as Peltier elements, on the applicator. Peltier elements cam be made of very compact design and can easily cover a temperature range of 20° C. temperature difference. Peltier elements may for example be provided on the inside of the distal gripper end 9, seen in the radial direction, it being of great advantage if the distal gripper ends 9, as well as the ring and gripper elements are made of a metal or ceramic material which conducts heat well. This is for a good conduction of heat/cold. At least one electrical power lead will have to be provided for the Peltier elements. With one electrical power lead, the applicator could even serve as another power lead. When using two power leads, basically no current needs to flow via the applicator itself. By switching the polarity of the Peltier element at a desired moment, the side of the Peltier element which contacts the distal gripper end 9 can first be cooled and then, after switching the polarity, heated. It will be clear that such a Peltier element or even another cooling system may also be provided elsewhere on the applicator. However, in that case, it is important that the applicator conducts the heat/cold well to the distal gripper ends. The response time of the temperature at the anchoring elements will in this case be slightly longer.

The influencing systems described before serve only as examples of possibilities which are all within reach of those skilled in the art. However, those skilled in the art will realize that other influencing systems are also possible. What is important is that the temperature of the anchoring elements in particular can be adjusted, in particular controlled.

With the assembly according to the invention, it is, by way of example, possible to proceed as follows:

the ring with anchoring elements in the fitting position is placed on the applicator, for example by means of loading devices to be described below with reference to FIGS. 7-8;

if necessary, the temperature of the anchoring elements is optionally temporarily brought to below the Martensitic finish temperature;

the anchoring elements are kept in the fitting position by cooling them to below the threshold temperature by means of the influencing system and/or by means of the sleeve 2, optionally with the tapering distal part connected thereto; in the absence of sleeve 2, the influencing system is preferably used to ensure that the anchoring elements have a temperature below the threshold temperature; however, if the threshold temperature is above ambient temperature and the body temperature of the patient during the operation, then neither the action of the influencing system, nor the sleeve 2 are required, although it is preferable to use one or both;

the applicator, in particular the distal end thereof, is transported to the intended position in the body of the patient;

if applicable, when it has reached the intended position inside the body of the patient, the sleeve 2, optionally with the tapering distal part connected thereto, is pushed up from the position shown in FIG. 1 to the position shown in FIG. 2; the ring with anchoring elements at the distal end is completely exposed; in order to facilitate shifting of the sleeve a pistol grip can be provided like the pistol grip as shown in FIG. 3 of applicant's earlier WO-03/003926. In case of a pistol grip one squeezes two handle parts towards each other in order to shift the sleeve or tapering distal part in proximal direction.

if required, the ring with anchoring elements will be positioned more accurately in the intended position;

if desired, the applicator may be temporarily fixed to the fixed surroundings, such as the sternum spreader, the operating table, or the fixed parts of the operating theatre;

once the ring with anchoring elements has been positioned sufficiently accurately in the intended position, a) the influencing system will be activated in order to raise the temperature of the anchoring elements to above the threshold temperature, as a result of which the anchoring elements turn over into the anchoring position, and b) the distal ends of the gripper arms 4 will be moved together in order to release the ring; in this case, phase a) increasing the temperature to above the threshold temperature, will preferably be carried out first, followed by phase b) releasing the ring, but this may optionally take place completely or partly simultaneously or, if circumstances require, even in reverse order;

the applicator is subsequently removed;

in case a vessel connection is intended, such as for example, a side-to-side anastomosis, the abovementioned actions will first be carried out at the location of the opening in the one vessel and subsequently on the other vessel on order then to connect both rings with one another. This connection can be achieved, for example, by pushing both rings "fixedly into one another", in the manner described above previously.

The shovel-shaped flat part 51 at the distal end of the central section 3 of the applicator is particularly useful if there is a valve prosthesis in the ring 8 which valve prosthesis has been arranged in the ring beforehand. The purpose of the flat shovel-shaped part 20 then is to keep the valve leaflets of the valve prosthesis still, in an open position, in order to reduce the risk of damage to these valve leaflets during execution of the implantation procedure, and preferably to avoid it altogether.

Figure 6A:
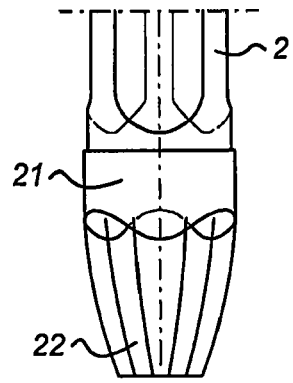
FIG. 6a shows a specific embodiment of the distal end of the protective sleeve, shown in particular in FIG. 3.
Figure 6B:
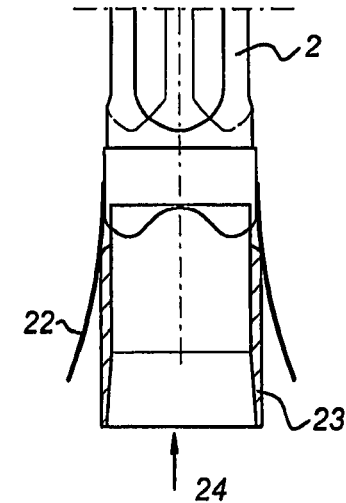
FIG. 6b shows a distal end of the protective sleeve from FIG. 6a with a loading tube inserted into it.

In order to facilitate moving the distal end of the applicator to the intended position inside the body of the patient, the distal end of the sleeve 2 may be provided—see FIG. 6a—with a distal part 21 comprising axial fingers 22 which can be bent outwards in the radial direction from the tapering position shown in FIG. 6—see FIG. 6b for this—in such a manner that this tapering part of the sleeve can be displaced over the ring for loading the ring onto the applicator which will be explained below, or for sliding the sleeve 2 upwards from the position shown in FIG. 1 to the position shown in FIG. 2 which has been explained above. The tapering distal part 21 facilitates navigation through the bloodstream or through other passages.

FIG. 6b furthermore shows a loading tube 23 which is placed between the axial fingers 22. When the loading tube 23 is removed, the axial fingers 22 will return to the shape shown in FIG. 6a The loading tube 23 assists in sliding a ring 8 with anchoring elements in the fitting position inside in the direction of the arrow 24 in order to attach this ring on the distal ends 9 of the gripper arms 4.

The tapering distal part 21 may also be connected to the bottom edge of sleeve 2 after the ring has been loaded in to the gripper arms 8 of the applicator and sleeve 2, following which part 21, from the proximal or distal direction, can be pushed over the distal part of the sleeve 21 and be fastened to it, for example by screws 3. This greatly facilitates loading using the loading tube 23 or directly using the loading device to be described below, as the axial fingers 22 then do not have to be spread or bent. In case no use is made of sleeve 2, the tapering distal part 21 or the loading tube 23 can also be used separately, as a means for keeping the bottom, and optionally the top, anchoring elements temporarily in the fitting position. If the ring has been placed on the applicator, the distal part 21 or the loading tube 23 may be removed immediately before positioning and the ring with the applicator can be positioned in the desired location, optionally using cooling to below the Martensitic finish temperature. Facilities may then be provided on the distal part 21 or the loading tube 23 and on the distal end of the applicator by means of which both components can be coupled to and uncoupled from one another. Another possibility is to use the tapering distal part 21 instead of using the sleeve and to load the ring into the distal part 21 from the axial side (the non tapering side) of the distal part. This can be done with a loading device like the one described below. This results in a space saving assembly enabling the operator to have a better view on the site of operation.

FIG. 7 highly diagrammatically shows an example of a loading device for loading a ring with anchoring elements in the fitting position into the applicator.

Figure 7A:
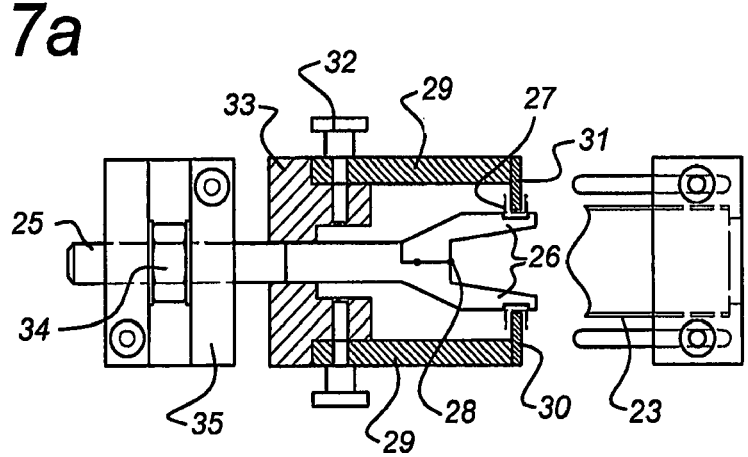
FIGS. 7a and 7b show a loading device for loading a ring with anchoring elements onto an applicator, with FIG. 7a showing the loading device in the initial position and FIG. 7b showing the loading device in an intermediate position.
Figure 7B:
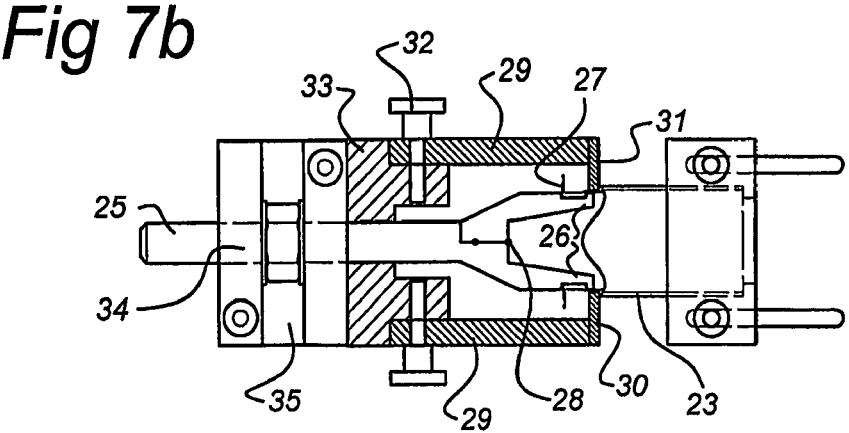

The loading device from FIG. 7 consists of a central gripper 25, comparable to the gripper arms 4 of the applicator. The ring with anchoring elements in the fitting position is placed on the gripper ends 26 of the gripper 25. The ring with anchoring elements in the fitting position is indicated by dashed lines in FIG. 7a and denoted by 27. In order to make it easier to push the gripper ends 26 through the ring, the gripper ends 26 are adjustable with respect to each other in the radial direction, for example can pivot about point 28. Subsequently, a flat—as opposed to cylindrical—ring 31, split into two parts 30 and 31, is placed from both sides between the radially protruding anchoring elements of the ring 27. Each split half ring is supported on a supporting arm 29. The supporting arms 29 are secured to a bush 33 by means of screws 32. Then, the anchoring elements on the right-hand side in FIG. 7a are extended into the fitting position by turning the nut 34. Turning the nut 34 results in the block 35 being placed against the bush 33 and in the gripper 25 being pulled inwards with respect to the split ring 30, 31. When the anchoring elements on the right-hand side in FIG. 7a have been extended, the loading tube 23 is placed against the split ring 30, 31. Subsequently, the nut 34 is turned in the opposite direction while the block is being held against the bush 33. The gripper 25 will then be withdrawn through the ring 30, 31 and slide into the loading tube 23. As soon as the split ring 30, 31 abuts the anchoring elements shown on the left-hand side in FIG. 7b—see in particular FIG. 7b, where they are still radially directed in the anchoring position—these left-hand anchoring elements 27 will be extended into the fitting position by the split ring 30, 31 in order to enable the ring 27 in the fitting position to be pushed entirely into the loading tube 23.

The ring with anchoring elements in the fitting position can then easily be placed on the carrier of the applicator. If appropriate, the ring with extended anchoring elements will first be subjected to a temperature treatment. This temperature treatment for freezing the anchoring elements in the extended position may, however, also take place after the ring has been loaded onto the applicator, and optionally be carried out by means of the applicator itself. In order to load the applicator, the loading tube 23 only has to be placed in line with the sleeve 2 or at least in line with the gripper arms 4, as is shown, for example in FIG. 6b. The gripper arms 4 can then be pushed into the loading tube 23 in order to grip the ring from the inside. Subsequently sliding the ring with gripper elements in the fitting position from the loading tube 23 into the sleeve 2 ensures that the anchoring elements remain in the fitting position. If the temperature of the anchoring elements is below the threshold temperature at the point in time when the ring is being transferred, the sleeve 2 is not strictly required, at least not for loading the ring with anchoring elements on the applicator. The distal end of the gripper arms 4 may, if appropriate, be brought to a low temperature, that is to say a temperature below the threshold temperature, in advance, in order to better ensure the anchoring elements remain "frozen" in the fitting position. As mentioned above, the loading device can also be used to load a fastening device or ring directly onto an applicator or into a sleeve, without using a separate loading tube 23.

Figure 8:
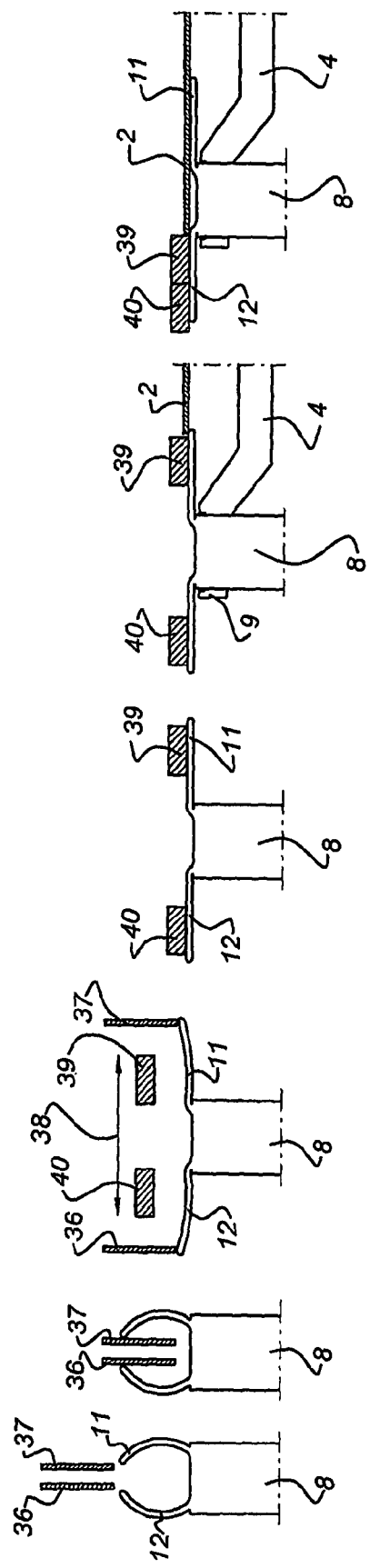
FIG. 8 shows the operation of an alternative loading device in a highly diagrammatic manner.

FIG. 8 highly diagrammatically shows another principle for a loading device which can be used with an assembly according to the invention. The steps in the loading process with the embodiment of FIG. 8 are shown from left to right. On the far left, a section of a ring 8 with anchoring elements 11 and 12 in the anchoring position is shown diagrammatically. Furthermore, two split flat rings 36, 37 are shown in the far left position, just above the anchoring elements 11 and 12, which rings 36, 37 are similar to the flat ring 30, 31 from FIG. 7. In this case, 36 and 37 in each case are one split part. The other split part has in each case not been shown. In a way similar to that of FIG. 7, the split rings 36, 37 are pushed between the anchoring elements 11, 12, as is shown in the second step from the left. The third step from the left shows how the split rings 36 and 37 are moved apart in accordance with arrow 38 in order to move the anchoring elements 11 and 12 from the anchoring position into an extended fitting position. This third step also already shows two pressure elements 39 and 40. These pressure elements 39 and 40 are pressed from the outside onto the anchoring elements 11, 12 in the fitting position, following which the split rings are removed. This leads to the phase shown as the fourth step from the left. Referring to the fifth step from the left, the distal ends 9 of the gripper arms 4 are inserted into the ring 8 in order to grip the ring from the inside. During this procedure, the distal end of the sleeve 2 is also pushed against the proximal pressure element 39. Then, as is shown in the step on the far right of FIG. 8, the gripper arms 4 are pulled into the sleeve 2, the sleeve 2 pressing the proximal pressure element 39 towards the distal pressure element 40 while the proximal anchoring elements 11 and the ring 8 are completely accommodated in the sleeve 2. Although it has not been shown, it will be clear that the gripper arms 4 are then further pulled into the sleeve 2 until the distal end of the sleeve 2 also overlaps the distal anchoring elements 12.

Figure 11A:
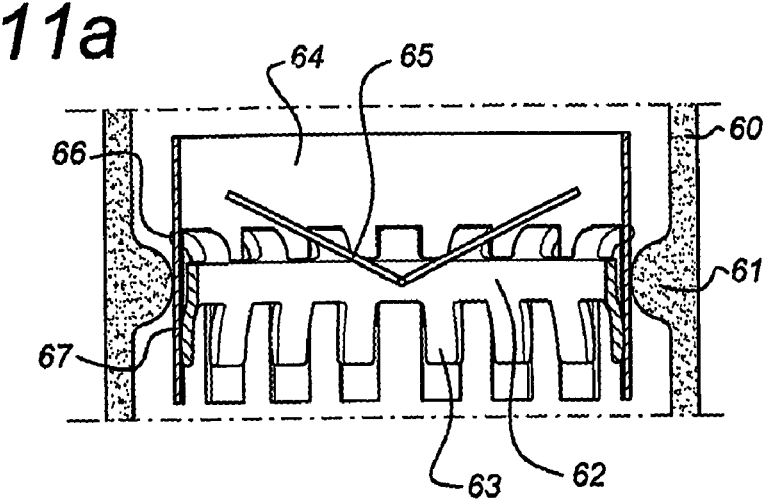
FIG. 11 shows a sectional view of a further embodiment of a sleeve or gripper which can be used with the assembly according to the invention in a position in which it carries the ring (FIG. 11a) and a position in which it releases the ring (FIG. 11b)
Figure 11B:
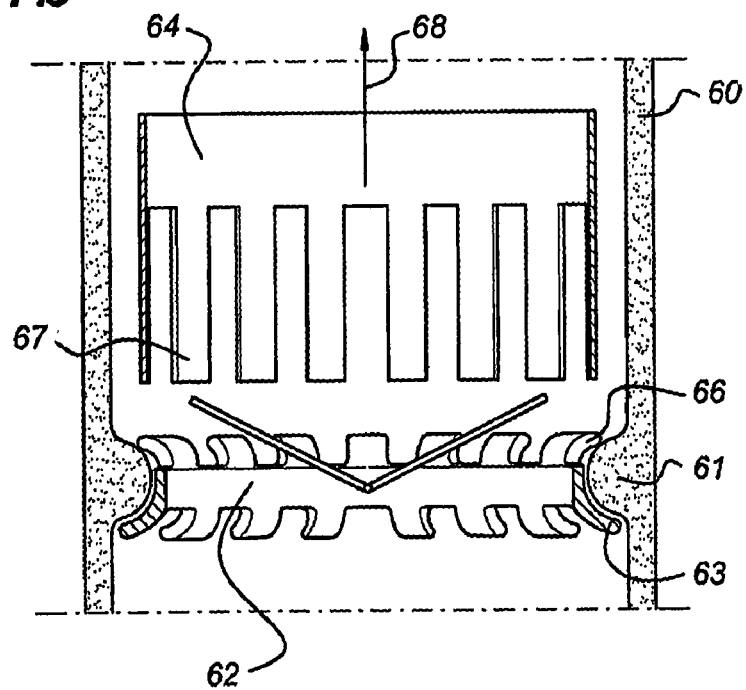

FIG. 11 diagrammatically shows an example of a sleeve of different design—as an alternative, for example, to sleeve 2 from FIG. 3 in which the gripper arms are (may be) present, but have not been shown here—or a gripper of alternative design—as an alternative, for example, to the gripper as shown in FIG. 5, in which case the sleeve in the embodiment of FIGS. 1-5 could be omitted and in which case some sort of retaining element is needed in order to keep the ring in place with respect to the blood vessel tissue when the gripper which is designed as a sleeve is being pulled back. FIG. 11 shows only the distal lower end of the sleeve or gripper (referred to below as sleeve/gripper). FIG. 11a shows the state in which the sleeve/gripper 64 accommodates the ring 62 in the fitting position, FIG. 11b shows the situation where the sleeve/gripper 64 has released the ring 62.

Referring to FIGS. 11a and 11b, it can be seen that the sleeve/gripper 64 has axial fingers 67 at its distal lower end. Furthermore, it can be seen that the ring 62 has distal anchoring elements 63 and proximal anchoring elements 66. In this case, the proximal anchoring elements are immovable and permanently directed in a radially outward direction. In this case, the proximal anchoring elements 66 and distal anchoring elements 63 are staggered with respect to one another. In the position shown in FIG. 11, the axial fingers 67 protrude through the proximal anchoring elements 66 in order to overlap and thus protect the distal anchoring elements 63 and to ensure that they are kept in an extended position at all times as long as the sleeve/gripper 64 is not withdrawn in accordance with arrow 68.

In addition, in FIG. 11*a* reference numeral 60 denotes a blood vessel, 61 an annulus, such as is present around the natural heart valve, and 65 an artificial heart valve. With respect to the artificial heart valve 65, it should be mentioned that this can already be present in essentially every embodiment of the ring as described above.

Figure 12A:
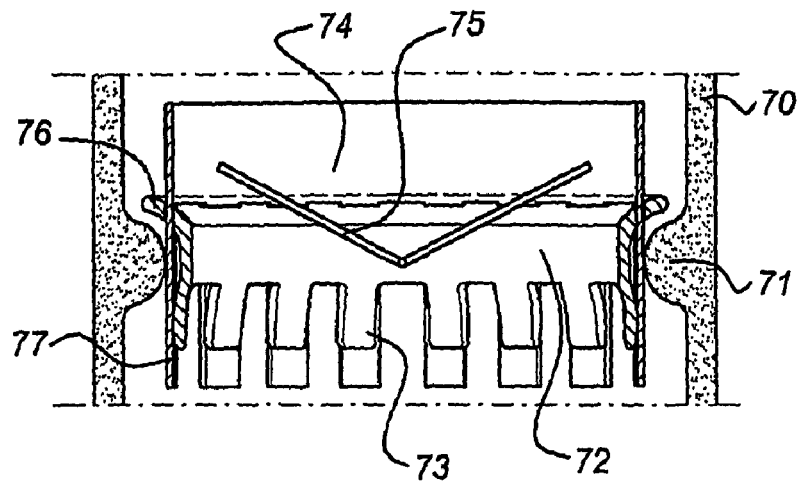
FIGS. 12a and 12b show a variant of FIG. 11a and FIG. 11b, respectively.
Figure 12B:
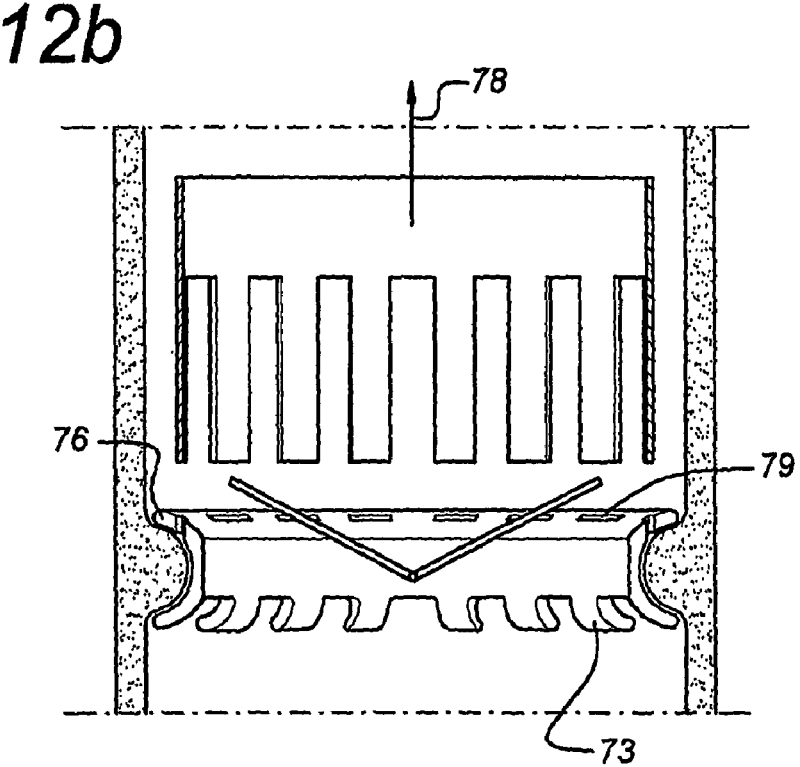

FIG. 12 shows a variant of FIG. 11, FIG. 12*a* corresponding to FIG. 11*a* and FIG. 12*b* corresponding to FIG. 11*b*. Similar parts are denoted by the same reference numerals as in FIG. 11, but increased by 10. The difference between FIGS. 11 and 12 essentially is that in FIG. 12, the proximal anchoring element is an uninterrupted, radially outwardly extending flange. In order to make space for the axial fingers 77 of the sleeve 74, a number of slots 79 are provided at the bottom of the flange 76 in the circumferential direction, into which the axial fingers 77 can be inserted.

With reference to that which is shown in FIGS. 11 and 12, it should be noted that an assembly of this type of, on the one hand, a sleeve/gripper and a ring with anchoring elements, on the other hand, may readily be used without the influencing system for influencing the temperature and without the anchoring elements being made of a memory material. The anchoring elements, in particular the distal anchoring elements, may for example equally well be made of a standard resilient material which does not have to be memory material at all. In this context, it will be clear that an assembly of a sleeve/gripper on the one hand and a ring with anchoring elements on the other hand, as shown in FIGS. 11 and 12 may also readily be employed in combination with the previous PCT applications by the inventor, i.e. WO 00/24339, WO 00/44311, WO 03/003926 and/or WO 03/082121.

After the fastening device has been attached, there may be space between or through the legs of anchoring elements 63, 66 and 73, via which leaks may occur, both of blood coming from above, as well as from blood coming from below the ring. The risk of such leaks can be reduced by inserting and attaching the ring in the annulus tissue under a certain tension, so that this tissue will completely or partially seal the space between the legs. In addition, after the axial fingers 67 in FIG. 11 and axial fingers 77 in FIG. 12 are removed, blood leaks may occur between the top anchoring elements 66 in FIG. 11 or through slots 79 in FIG. 12. For these reasons, it is advantageous according to the invention, if the anchoring elements and/or fixed top flange are coated with textile, this coating not only covering the anchoring elements themselves, but also the space at the location of the slots 79 and between the anchoring elements, completely or partially, or even beyond their periphery. At the location of the spaces between the top anchoring elements 66, such a textile coating may temporarily be pressed out of the way by the axial fingers 67. Once the axial fingers 67 are withdrawn, the coating takes up this space again. In the case of slots 79, similar openings can be made in the coating of the top flange through which the axial fingers 77 are temporarily moved up. Once these axial fingers are withdrawn, the coating takes up this space again. Such an elastic motion by the coating can, inter alia, be achieved by producing the coating from elastic material, such as for example plastics like Dacron or Teflon, such as are currently already being employed in suture rings for valve prostheses. It is also possible to provide an additional textile edge which is free on the lateral side in the middle of the openings between the anchoring elements 66 and slots 79, if desired even close to the transition from the ring to the valve, which, in case this textile edge is arranged on the upper side of the ring, will be pushed downwards by the bloodstream and, in case this textile edge is arranged on the underside of the ring, will be pushed upwards by the bloodstream, in both cases resulting in a seal. In the text above, textile coating is intended to mean, inter alia, materials such as are being used in the production of suture rings for valve prostheses, but a textile coating may also consist of other deformable elastic biocompatible materials. A coating of this type may consist of multiple layers, optionally supplemented by materials which serve as an optionally elastic filling in order to achieve the desired shape or mechanical effect.

With reference to that which is shown in FIGS. 11 and 12, it will furthermore be clear that, although that which has been shown in FIGS. 11 and 12 relates to a heart valve prosthesis, this may equally well be applied in attachment devices for performing an anastomosis, such as those which have been described in the abovementioned four PCT applications by the inventor. To this end, reference is made by way of example to FIG. 14, which is very similar to FIG. 8 from WO 00/24339, which relates to an attachment device 100 for performing an end-to-side anastomosis. Reference may be made to WO 00/24339 for details of an attachment device of this type. In this case, 103 is a cylinder sector-shaped flange which is applied to the target vessel from outside. 104 denotes anchoring elements, referred to as bottom flange legs in WO 00/24339, which can turn over in a radially outward direction by the effect of a spring force, optionally assisted by the action of a memory metal, in such a manner that the wall of the target vessel is clamped between the anchoring elements 104 and the cylindrical part 103. A raised ring with holes 106 therein is provided on the cylindrical part 103, around the passage 105 formed therein, in order to be able to attach a graft blood vessel to the ring 107 using suture thread.

With reference to FIG. 12 and the additional pins 120 of FIG. 15 (described further below), it is to be noted that the anchoring of the ring 72 to the annulus can be improved by providing the fixed flange 76 at its underside with anchoring pins. Those anchoring pins extend in the insertion position axially in order to facilitate easy penetration of the annulus, this is called the first penetration position. The anchoring is improved when, after piercing the pin 120—like shown on the left side of FIG. 15—straight and axially into the annulus, this pin is bend in an arbitrary direction to a second penetrated position. By providing such a bend the pin will less easily come loose from the annulus. Although FIG. 15 shows, at the right side, the pin 120 bend in radially inward direction, this bending direction can for just anchoring also be different, for example in radially outward direction or in tangential direction or a direction in between. The stronger the bend of the pin, the stronger the anchoring effect. With reference to FIG. 12, one could provide pins 120 directly adjacent the small side of a slot 79. By bending the pin then from a tangentially curved direction—in which it extends in front of the slot—to an axially straight direction and inserting the fingers 77 through the slots 79, the fingers keep the pins 120 in the first position ready for penetration into the annulus. Withdrawing the fingers will then firstly allow the lower flange 73 to bend outwards—when the temperature exceeds the threshold—and secondly allow the pins to return to the tangentially curved direction to extend in front of the slots 79 again. The pins can return to this position by using memory shape effects as discussed earlier or just by using normal spring bias effects coming free when a mechanical constraint (the fingers) is removed. It will be clear that the pins can also be arranged adjacent the longer sides of the slots when it is desired to allow the to bend in radially inward or outward direction. Further, it will be clear that this additional anchoring effect can also be used with applicants earlier inventions as described in WO-00/24339, WO-00144311, WO-03/003926 and WO-03/082121, without the first invention or the second invention of this application being applied.

In addition, FIG. 14 shows approximately half of a cut-away sleeve 101 with axial fingers 102 at its distal lower end. The axial fingers 102 are in this case shown excessively long for the purposes of clarity of the drawing. It will be clear that the axial fingers 102 can be shortened to a length which is approximately that of the anchoring elements 104. Slots 108 are formed in the cylinder sector-shaped part 103, through which the axial fingers 102 can protrude in order to block the anchoring elements 104 from the outside. As soon as the sleeve 101 is withdrawn in an upward direction in accordance with arrow 110, the anchoring elements 104 will be able to fold out in order to clamp tissue from the wall of the target vessel against the cylinder sector-shaped part 103. As has been described before regarding the shape and distribution of the anchoring elements 104, it may furthermore be advantageous to accordingly give the axial fingers 102 a different shape, length and width and to distribute them unevenly over the circumference of the ring. It will be clear that the principle of attaching a vessel attachment device of this type can also be applied to bring about a side-to-side anastomosis, in which case a vessel attachment device of this type is fitted at the location of the opening in the side wall of the two vessels concerned in the manner shown. These two vessel attachment devices can now be coupled to one another in mirrored or preferably parallel manner. In order to actually bring about the coupling of both vessel attachment devices in mirrored manner, facilities can be arranged on the attachment device around opening 105. For example, a ring in the shape of a flat disk 107, optionally extending over the entire circumference, optionally provided with slots 108, having a 'female' or 'male' shape. In the case of the parallel coupling, it is preferable to use the cylinder-shaped parts 103 of both vessel attachment devices themselves. This is made easier if the raised ring 107 is omitted and lateral extensions are provided on, for example, the lateral edges of the cylinder sector-shaped part 103 of at least one of the two vessel attachment devices, which provides this part with wings, as it were. The cylinder sector-shaped part 103 or the lateral extensions thereof of both or at least one of the two vessel attachment devices can be treated by deforming it or by punching openings into it. Examples of such treatments are bending, rolling up or providing the material with corners. By treating both vessel attachment devices in a different manner, it is possible to turn the one cylinder sector-shaped part 103 into a receiving 'female' part and the other cylinder sector-shaped part 103 into an insertable 'male' part. In this manner, it is possible to press the cylinder sector-shaped parts 103 of the two vessel attachment devices together and/or hook them up and attach them to one another. Those skilled in the art will know many ways of connecting the two vessel attachment devices. It is also possible to impart or apply a different magnetic charge to each of the two cylinder sector-shaped parts 103, to glue both parts together, or to secure them or clip them with one or more additional components. A further advantage of connecting two vessel connecting devices in a parallel manner is that any blood leakage through slots 108 after the removal of the axial fingers 102 is prevented. With a mirrored coupling, it is possible to arrange an additional ring around the opening 105 over slots 108. With an end-to-side anastomosis, sealing of the slots 108 can be achieved by using a coupling piece overlapping these slots on the graft vessel, as is known from previous applications by the Applicant. Slots 108 or other openings in the cylinder sector-shaped part 103 can also be used to apply a vacuum through, in order to temporarily achieve a good tissue contact between the attachment device and the tissue. The use of vacuum in such situations has been described in previous applications by the inventor.

FIG. 13 highly diagrammatically shows an example of an influencing system which comprises a source for generating an alternating electromagnetic field. 80 denotes a vessel wall, 81 the annulus of a heart valve, 82 a ring provided with distal anchoring elements 83 and proximal anchoring elements 84 and 85 denotes an artificial heart valve. The ring 82 and anchoring elements 83 and 84 are made of memory metal, such as Nitinol, that is to say at least the ring 82 and anchoring elements 83, 84 comprise a memory metal. For the sake of clarity, the applicator has been entirely omitted from FIG. 13. A sleeve which may optionally be used with the applicator may already have been withdrawn prior to the temperature-influencing operation to be described below or may be withdrawn subsequent to the temperature-influencing operation to be described below. During the temperature-influencing operation to be described below, the ring 82 will preferably still be securely held by a gripper in order to keep it in place, though.

The temperature-influencing operation by means of a source for an alternating electromagnetic field can be effected by placing a loop 89, indicated diagrammatically in FIG. 13a, with connecting ends 91 and 92 and bending it back around the blood vessel 80 as has been indicated in FIG. 13a in section. The loop 89 can be placed around the blood vessel 80 as the connecting ends 91 and 92 allow the loop to be bent open or otherwise by designing the loop, for example split. The split embodiment can be achieved by providing a plug-and-socket connection for the one sleeve part and for the other sleeve part at the location of the reference numeral 93. The loop 89 is connected to the alternating current source 90 by means of the connecting ends 91, 92. This alternating current source will create an alternating electromagnetic field in the loop which, inside the loop, is directed in particular in the direction of arrow 94 and will be highly concentrated in said location. This results in the ring 82 comprising memory metal and anchoring elements 83 and 84 heating up in a very short time to above the threshold temperature. As soon as the threshold temperature is exceeded by a sufficient amount, the distal anchoring elements 83 will fold out in accordance with arrow 86 and the proximal anchoring elements will fold out according to arrow 87 in order to fasten the ring 82 to the annulus 81. It will be clear to those skilled in the art that by means of FIG. 13 only an example of an influencing system working by means of an alternating electromagnetic field has been described. It is, for example, not strictly necessary for the loop 89 to be laid around the blood vessel 80. The loop 89 may also positioned next to the blood vessel or in the lumen of the blood vessel above and/or below the ring. Furthermore, it is entirely conceivable for the loop 89 to be replaced by a coil having a number of loops. In addition, as those skilled in the art will realize, it is not necessary to use a loop for generating an electromagnetic field. This may also be achieved by other methods known from the prior art.

Figure 15A:
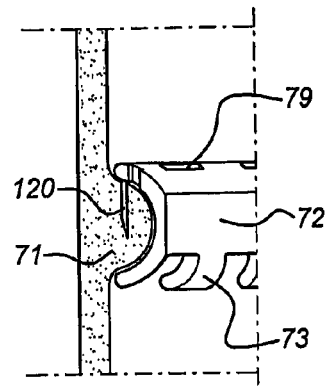
Figure 15B:
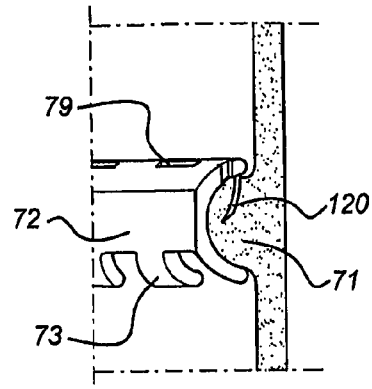
Figure 16A:
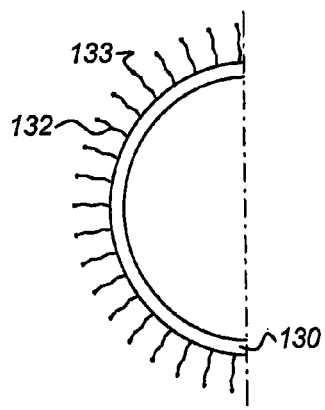
Figure 16B:
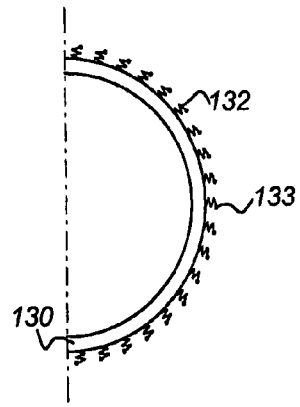
Figure 16C:
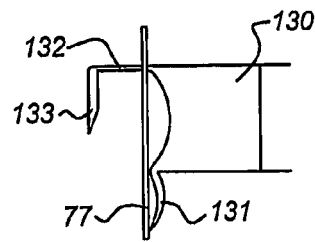
Figure 16D:
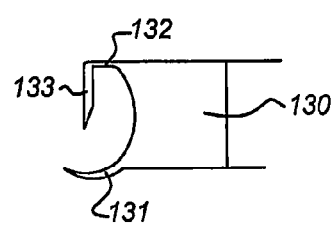

FIG. 15 shows the second invention in a first embodiment. FIG. 15 is essentially based on FIG. 12. The sleeve 74 with fingers 77 and valve leaves 75 are no shown. Further same reference numbers as in FIG. 12 are used. It is shown that the pins 120 lie adjacent the outer, longer side of the slots 79. The pins are in straight position (FIG. 15a), called the first penetrated position, prebiased towards the bend position, called the second penetrated position, as shown on the right of FIG. 15 in FIG. 15b. Although here the fingers 77 of the sleeve are mentioned as mechanical constraints, it is to be noted that those fingers 77 and the corresponding slots 79 can be left away, when one uses the memory shape effect of suitable metals or plastics to keep the pins in straight position and allow them to return to the bend position after increasing the temperature above a certain threshold. As the pins move radial inward—according to FIG. 15 by bending—only after they have been fully pierced into the annulus, this movement is fully utilized to press the annulus correspondingly in radial inward direction, the annulus is so to say constricted (although its diameter might be unchanged because the ring 72 actually prevents the annulus from restriction.

FIG. 16 shows that the pins can also be arranged to be able to move radially inward by means of another construction. FIG. 16 shows a ring member 130 carrying valve leaflets (not shown). The ring 130 is provided with a lower flange 131 which can bend from straight axial position to radial position to lie against the underside of a valve annulus (not shown). The ring 130 is also provided with an upper flange 132, which can like lower flange bend from an axial straight position to a radial position, but which can also, as shown, be permanent in radial extending position. The upper flange comprises arm segments 132 extending essentially radial. Those arm segments 132 carry at their ends pins 133. The arm segments 132 are arranged so that they can shorten by returning under influence of shape memory effects or otherwise to a shortened condition in which they have a zig-zag-like shape. For improving the anchoring effect it is conceivable to allow the pins 133 to bend as well, see discussion above at the end of FIG. 12.

It is also conceivable—see FIG. 17—to arrange for a separate constriction ring 121, which is to lie around the ring member 72 of a valve prosthesis, preferably in between the lower 73 and upper 76 flanges as invented earlier by applicant, see WO-00/24339, WO-00/44311, WO-03/003926 and WO-03/082121

The invention claimed is:

1. Heart valve prosthesis comprising:
a ring member for attachment to a valve annulus; and
a constriction system comprising anchoring pins for penetrating into the valve annulus,
wherein the anchoring pins have a straight first position and a second position;
wherein, in the first position, the anchoring pins extend in an axial direction;
wherein the anchoring pins are arranged around the circumference of the ring member and are adapted to move, after the anchoring pins have fully penetrated into the valve annulus from the first position in a radially inward direction with respect to the ring member, to the second position, to press the annulus correspondingly in the radially inward direction;
wherein the ring member comprises a lower flange which is bendable from a straight axial position to a radially outward position with respect to the ring member, and an upper flange having a radial outwardly extending position with respect to the ring member, and
wherein, when the lower flange is in the radially outward position, the anchoring pins are arranged between the upper and lower flange.

2. Prosthesis according to claim 1, wherein the anchoring pins are bent from the second position into the first position against a spring force and are fixed in the first position in a releasable manner such that upon release the anchoring pins return to the second position.

3. Prosthesis according to claim 2, wherein the constriction system further comprises a carrier, and wherein the anchoring pins are arranged on the carrier which is adapted to shorten such that the anchoring pins move in said radially inward direction.

4. Prosthesis according to claim 3, wherein the prosthesis comprises memory metal or memory plastic frozen in the first position to be released to go back to the second position when the temperature increases above a threshold temperature.

5. Prosthesis according to claim 3, wherein the carrier comprises a radial arm for each said anchoring pin, which radial arm can be shortened by memory effects of memory metal or memory plastic.

6. Prosthesis according to claim 3, wherein the carrier comprises a carrier ring adapted to be reduced in diameter by use of memory effects of a memory metal or memory plastic.

7. Prosthesis according to claim 2, wherein the prosthesis comprises memory metal or memory plastic frozen in the first position to be released to go back to the second position when the temperature increases above a threshold temperature.

8. Prosthesis according to claim 1, wherein the constriction system further comprises a carrier, and wherein the anchoring pins are arranged on the carrier which is adapted to shorten such that the anchoring pins move in said radially inward direction.

9. Prosthesis according to claim 8, wherein the carrier comprises a radial arm for each said anchoring pin, which radial arm can be shortened by memory effects of memory metal or memory plastic.

10. Prosthesis according to claim 8, wherein the carrier comprises a carrier ring adapted to be reduced in diameter by use of memory effects of a memory metal or memory plastic.

11. Prosthesis according to claim 8, wherein the carrier comprises a carrier ring adapted to be reduced in diameter by use of memory effects of a memory metal or memory plastic.

12. Prosthesis according to claim 1, wherein the constriction system comprises a constriction ring element separate from the ring member and adapted to lie around the ring member.

13. Prosthesis according to claim 12, wherein the anchoring pins are bent from the second position into the first position against a spring force and are fixed in the first position in a releasable manner such that upon release the anchoring pins return to the second position.

14. Prosthesis according to claim 13, wherein the prosthesis comprises memory metal or memory plastic frozen in the first position to be released to go back to the second position when the temperature increases above a threshold temperature.

15. Prosthesis according to claim 12, wherein the anchoring pins are arranged on the constriction ring element and wherein the constriction ring element is adapted to shorten such that the anchoring pins move in said radially inward direction.

16. Prosthesis according to claim 15, wherein the constriction ring comprises a radial arm for each said anchoring pin, which radial arm can be shortened by memory effects of memory metal or memory plastic.

17. Prosthesis according to claim 1, wherein the ring member is provided with a material enhancing ingrowth of tissue.

18. Prosthesis according to claim 1, wherein the upper flange comprises arm segments extending essentially radially with respect to the ring member and carrying at their ends the anchoring pins, wherein the arm segments are arranged to shorten by returning under influence of a shape memory effect to a shortened condition in which the arm segments have a zig-zag-like shape.

19. Prosthesis according to claim 1, wherein the prosthesis further comprises one, two or more valve leaflets arranged inside the ring-member.

20. Prosthesis according to claim 1,
wherein, in the first position, the anchoring pins extend from the upper flange in the direction of the lower flange.

21. Prosthesis according to claim 1,
wherein the upper flange is a radially outwardly extending flange provided with slots;
wherein the prosthesis further comprises axial fingers inserted through said slots;
wherein the anchoring pins are provided at the underside of the upper flange adjacent a said slot so that the anchoring pins, kept in the straight first position by the axial fingers inserted through said slots, are allowed to move to the second position upon withdrawal of the axial fingers.

22. Heart valve prosthesis comprising:
a ring member for attachment to a valve annulus, and
a constriction system having anchoring pins for penetrating into the valve annulus,
wherein the anchoring pins are arranged around the circumference of the ring member and adapted to move in a radially inward direction with respect to the ring member, after the anchoring pins have fully penetrated into the valve annulus, from a first position to a second position to press the annulus correspondingly in the radially inward direction; and
wherein the ring member comprises a lower flange which is bendable from a straight axial position to a radially outward position with respect to the ring member, and an upper flange having a radial outwardly extending position with respect to the ring member, wherein the upper flange comprises arm segments extending essentially radially with respect to the ring member and carrying at their ends the anchoring pins, wherein the arm segments are arranged to shorten by returning under the influence of a shape memory effect to a shortened condition in which the arm segments have a zig-zag-like shape.

* * * * *